United States Patent

Johnston et al.

[11] Patent Number: 6,144,787
[45] Date of Patent: Nov. 7, 2000

[54] AIMING AND FOCUSSING DEVICE FOR FIBER-TRANSPORTED LASER RADIATION

[75] Inventors: Timothy J. Johnston, Mountain View; John L. Nightingale, Portola Valley, both of Calif.

[73] Assignee: Coherent, Inc., Santa Clara, Calif.

[21] Appl. No.: 09/072,483

[22] Filed: May 4, 1998

[51] Int. Cl.[7] ............................... G02B 6/26; G02B 6/32
[52] U.S. Cl. .............................. 385/31; 385/33; 385/117; 385/902
[58] Field of Search .................................. 385/31, 33–35, 385/117, 902; 606/16; 607/93

[56] References Cited

U.S. PATENT DOCUMENTS

| | | | |
|---|---|---|---|
| 4,215,937 | 8/1980 | Borsuk | 356/73.1 |
| 4,458,683 | 7/1984 | Saito et al. | 606/3 |
| 4,761,054 | 8/1988 | Ishimori et al. | 385/117 |
| 4,898,444 | 2/1990 | Grimes et al. | 385/31 |
| 5,031,980 | 7/1991 | Colles et al. | 385/123 |
| 5,394,492 | 2/1995 | Hwang | 385/33 |
| 5,625,459 | 4/1997 | Driver | 356/446 |
| 5,815,627 | 9/1998 | Harrington | 385/125 |

*Primary Examiner*—Rodney Bovernick
*Assistant Examiner*—Michael J. Stahl
*Attorney, Agent, or Firm*—Limbach & Limbach L.L.P.

[57] ABSTRACT

Apparatus (20) for aiming and projecting laser radiation emitted from an output-face (56) at an output-end (52) of an optical-fiber transmitter (54), includes a target (26) surrounding the output-end of the optical-fiber transmitter and held in a fixed relationship therewith. One or more light sources (46) illuminate the target with visible light such that the target directs at least a portion of the visible light in the emission direction of the laser radiation whereby when the optical-fiber transmitter is directed toward a surface, the visible light directed by the target indicates an incidence region of the laser radiation on the surface. The apparatus optionally includes an optical system (27) arranged to project a visible image (72) of the target and an image (74) of the output-face of the optical fiber transmitter. The degree of focus of the visible target-image on the surface corresponds to the degree of focus of the laser radiation on the surface.

26 Claims, 6 Drawing Sheets

AIMING AND FOCUSSING DEVICE FOR FIBER-TRANSPORTED LASER RADIATION

TECHNICAL FIELD OF THE INVENTION

The present invention relates in general to delivery of laser radiation. It relates in particular to aiming and focussing laser-radiation which is transported by an optical-fiber or a bundle of optical-fibers.

DISCUSSION OF BACKGROUND ART

Optical-fibers or bundles of optical-fibers, are commonly used to transport laser radiation from a laser source to a site at which it will be used. Uses may include, for example, medical uses, such as laser treatment of pigmented skin lesions, photodynamic therapy, laser depilation, and industrial uses such as drilling, marking or heat-treating material.

Typically laser radiation exits an optical-fiber or optical-fiber bundle as a diverging beam. This beam often is focussed by one or more optical elements connected with the fiber bundle to a spot of a size appropriate for a particular use. In many applications, it may be impractical, if not impossible, for a user to detect the focus of such optical elements and locate a point at which the radiation is to be delivered, i.e., aim the laser radiation by the light of the laser radiation itself.

Such applications would include applications wherein the laser radiation was being delivered at an intensity too great to be delivered in an uncontrolled or erratic manner, whether the radiation was being delivered in the form of short-pulses or quasi-continuously. Such applications would also include, of course, applications in which radiation being delivered were in the ultraviolet or infrared spectral regions and thus invisible to the human eye.

One simple means of focus location and aiming would be to provide a mechanical spacer or probe device attached to the optical elements which could make contact with a surface to which the laser radiation was to be delivered. Contact would occur when the optical elements were at a focal distance from the surface. Such a spacer or probe, suitably aligned with the optical elements and optical-fiber bundle, could also include an aperture which indicated where radiation would be delivered on the surface. Such a system has several disadvantages. By way of example, it would be undesirable for use with materials which would be easily marred or distorted by contact such as thin glass or plastic materials. A mechanical system, particularly an aperture may interfere with an operator's view of a surface to be treated. Further an aperture in the path of laser radiation may be subject to heating and possible damage by the laser radiation.

One optical means of focussing and aiming laser radiation from a fiber bundle is described in U.S. Pat. No. 5,394,492 to Hwang, which discloses a high power semiconductor (diode) infrared laser system. In this system, the output of an array of individual diode-lasers is collected by coupling the output of each into an input end of an optical-fiber associated therewith and collecting the output-ends of the fibers into a bundle. One or more refractive optical elements are provided for focussing a diverging beam delivered by the bundled output-ends of the fibers. A system for aiming and focussing the beam is taught, wherein at least one of the diode-lasers emits light in the visible spectrum, and the fiber associated with that diode-laser is bundled with the remaining fibers. This provides that some portion of the beam output from the bundled fibers is visible, allowing the beam to be aimed and focussed.

While the aiming and focussing system of the Hwang patent is doubtless effective in certain applications, it requires that a laser array be specially configured to provide an aiming and focussing beam. This can significantly increase the cost of manufacturing and assembling the array. Further, given a constant total number of diodes in an array, the greater the number of diodes emitting visible light for aiming purposes, the less will be available for delivering infrared power for the application. Further, diode lasers are available only in a limited range of colors, primarily red.

There is a need for an aiming and focussing system for optical-fiber-delivered radiation which can be independent of a laser device or array providing the laser radiation to be delivered. Preferably the system should be capable also of providing a variety of aiming targets differing, for example, in shape or color.

SUMMARY OF THE INVENTION

The present invention is directed to apparatus for aiming and projecting laser radiation emitted from an output-face of an optical-fiber transmitter. The term "projecting", in this specification and the appended claims, is intended to include focussing radiation emitted from the output-face of an optical-fiber transmitter to a point or relaying an image of the output-face of the optical-fiber to a surface where the laser radiation is to be used. The term "optical-fiber transmitter" is intended to include a single fiber or a fiber bundle.

In one aspect, the apparatus comprises a target held proximate the output-face of the optical-fiber transmitter in a fixed relationship therewith. At least one light-source is directed at the target for illuminating the target with visible light.

The target and light-source are arranged such that the target directs at least a portion of the visible light in the emission direction of the laser radiation in such a way that, when the optical-fiber transmitter is directed toward a surface, the visible light directed by the target indicates an incidence point of the laser radiation on the surface.

In another aspect of the present invention, an optical system of one or more optical elements may be aligned with the output-face of the optical-fiber transmitter and the target, and arranged to project a visible image of the target and an image of the output-face of the optical-fiber transmitter. The visible target-image on the surface indicates an incident point (region or area) of the laser radiation. The degree of focus of the visible target-image corresponds to the degree of focus of the laser radiation. Accordingly, focussing the target-image on the surface by varying the distance of the apparatus therefrom, automatically focuses the laser radiation on the surface. The optical system may be a focussing system, a magnifying system, a reduction system, or a variable magnification or reduction (zoom) system. Preferably, the target is configured such that its image surrounds or encircles the image of the output-face of the optical-fiber transmitter, for example, in the form of a circle or a cross centered on the image of the output-face of the optical-fiber transmitter.

In yet another aspect of the present invention, the above-described apparatus may be arranged such that the output-face of the optical-fiber transmitter is removably held in alignment with the target. This provides that the one such apparatus may be useable with a number of optical-fiber transmitters, or that differently configured variations of the inventive apparatus may be used with one optical-fiber transmitter.

In one preferred embodiment of apparatus in accordance with the present invention, the target is a cylinder of translucent or diffusely transmissive material surrounding the output-end of the optical-fiber transmitter. The output-end of the optical-fiber transmitter is inserted through the cylindrical target with the output-face of the optical-fiber transmitter aligned with the distal end of the cylindrical target. The cylindrical target is illuminated by a plurality of light-emitting diodes (LEDs) radially arranged around the cylindrical target, with the output axis of each of the LEDs inclined toward the distal end of the target. Light from the LEDs is collected by the target and transmitted, by a light-piping effect along the target, and emitted therefrom in the emission direction of laser radiation from the optical-fiber transmitter.

Apparatus in accordance with the present invention is particularly useful in applications wherein the laser radiation is to be delivered at an intensity too great to be delivered in an uncontrolled or erratic manner, or when the radiation to be delivered is in the ultraviolet or infrared spectral regions and thus invisible to the human eye. The apparatus is useful whether the radiation is to be delivered in the form of pulses, continuously or quasi-continuously.

One particular advantage is that one such apparatus may be used with a number of different delivery systems. Alternatively, different forms of the apparatus may be used with the same delivery system.

As LEDs are now available in a wide range of spectral colors, use of LEDs as light sources for providing target illumination provides that almost any target color can be selected to suit a particular application. This can be important, for example, in photodynamic therapy, where activation wavelengths for the therapy are typically in the visible spectrum. Here it would usually be undesirable for target light to be of a wavelength at, or even close, to a stimulating wavelength.

The above described uses and advantages of the present invention are merely examples, and should not be considered limiting. Other uses and advantages will become evident to those skilled in the art from consideration of the detailed description of the invention set forth below.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

Turning now to the drawings, wherein like components are designated by like reference numerals, FIG. 1, FIG. 2, FIG. 3 and FIG. 4 schematically illustrate a preferred embodiment 20 of aiming and focussing apparatus in accordance with the present invention. Apparatus 20 includes an optics housing 22 which has, at a proximal end 22A thereof, a target support 24 on which is supported a cylindrical target 26. Cylindrical target 26 is preferably formed from a diffusely-transmissive or translucent material. By way of example, the target may be fabricated from glass, plastic or ceramic materials that are at least partially transparent to visible light. Further, as will be described further hereinbelow, the use of completely transparent materials is not precluded. At a distal end 22B of optics housing 22 is an optical system 27 including two plano-convex lens elements 28 and 30. Target 26, and optical elements 28 and 30 are aligned on an optical axis 32.

Figure 1:
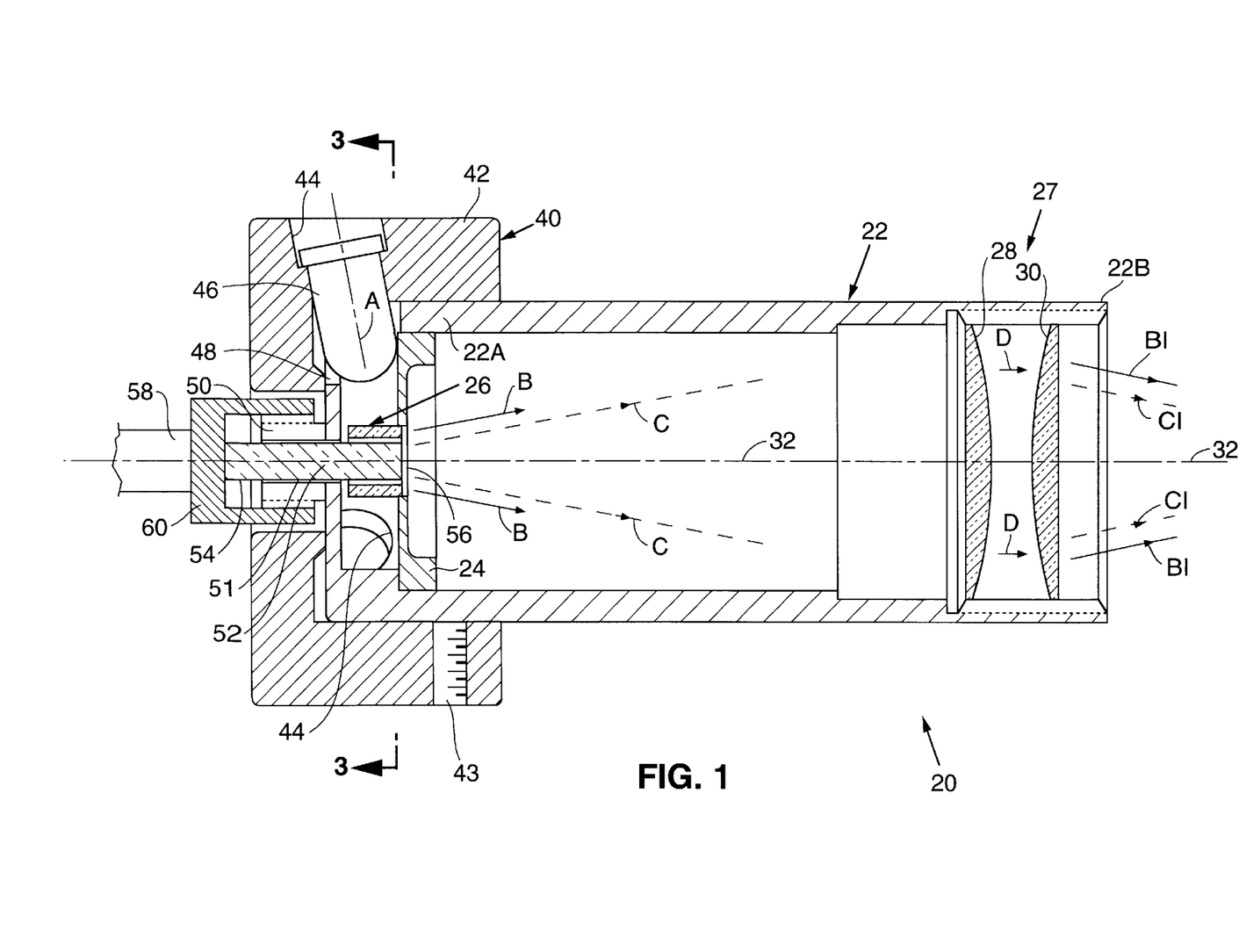
FIG. 1 is a view partly in cross-section schematically illustrating one preferred embodiment of aiming and focussing apparatus in accordance with the present invention, including an optics housing, a cylindrical target located in the optics housing, an illuminator for illuminating the target, and an optical system in the optics housing for forming an image of the illuminated target and the output-face of an optical-fiber transmitter held adjacent the target.
Figure 2:
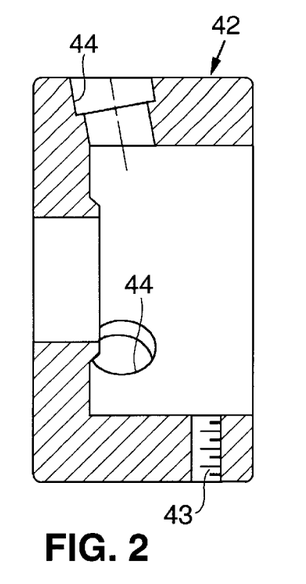
FIG. 2 is a cross-section view schematically illustrating details of a housing of the illuminator of FIG. 1, including a radial array of light emitting diodes arranged to direct light therefrom toward the target of FIG. 1.
Figure 3:
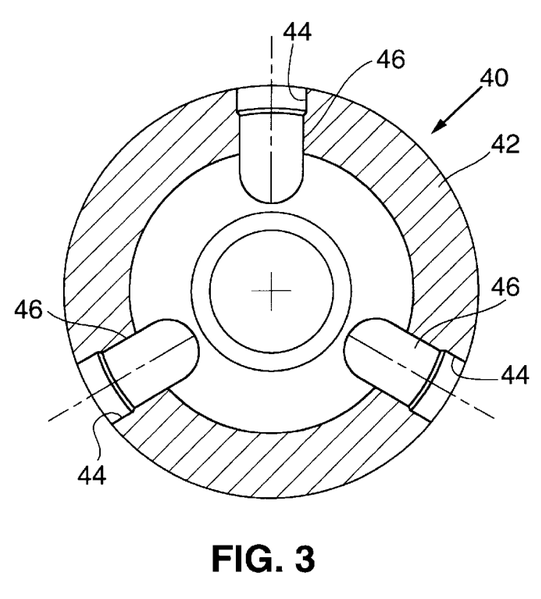
FIG. 3 is a cross-section view seen generally in the direction 3—3 of FIG. 2 schematically illustrating further details of the illuminator of FIG. 1, including a radial array of light-emitting diodes arranged to direct light therefrom toward the target of FIG. 1.
Figure 4:
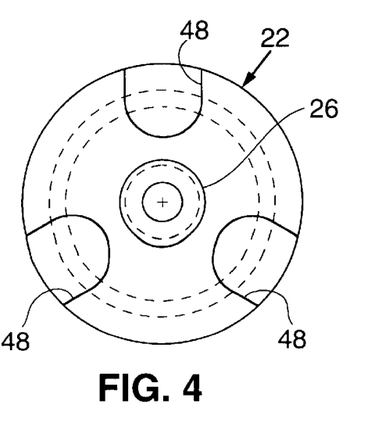
FIG. 4 is an end-elevation view of the optics housing of FIG. 1, schematically illustrating details of aperture therein for accepting the light-emitting diodes of FIG. 3.

Fitted over proximal end 22A of optics housing 22 is an illuminator 40 having an illuminator housing 42. Illuminator 40 is held in place on optics housing 22 by a set screw 43. Illuminator housing 42 has three apertures 44 therein, radially arranged therearound. Each aperture 44 is configured to accept an LED 46. Only one LED is shown in FIG. 1 for clarity. Preferably all three apertures 44 include an LED as illustrated in FIG. 3. Apertures 48 in proximal end 22A of optics housing 22 provide access for LEDs 46 to the interior of optics housing 22. Wiring and power supplies for LEDs 46 are well known to those skilled in the art to which the present invention pertains and a description thereof is not necessary for understanding principles of the present invention. Accordingly, description and depiction of such wiring are not presented herein.

LEDs are preferred light sources for illuminator 40, among other reasons, because they are highly efficient and provide high light output in a small volume. It should be noted, however, that light sources of the present invention are not limited to LEDs but may include without being limited to, incandescent-sources, electroluminescent panels, and diode lasers.

Further, it should be noted that while LEDs 46 are depicted in apparatus 20 as pointing directly at the target, those skilled in the art may devise other illuminating arrangements, wherein light sources do not point directly at the target, without departing from the spirit of the present invention. In such arrangements, for example, light from the light sources may be directed to target 26 by prisms, mirrors, diffusers, or the like.

Axially arranged on proximal end 22A of optics housing 22 is a male connector-member 50 having an aperture 51 extending axially therethrough. An output-end 52 of an optical-fiber transmitter 54 extends through male connector-member 50 and target 26 with output-face 56 thereof aligned with the end of target 26. Outside of illuminator 40, optical-fiber transmitter 54 is surrounded by a flexible sheath 58. A female-connector member 60, attached to sheath 58, removably engages male connector-member 50. This removably holds output-end 52 and output face 56 of optical-fiber transmitter 54 in a fixed spatial relationship and alignment with target 26 and optical system 27.

It should be noted here that optical-fiber transmitter 54 is illustrated in FIG. 1, for clarity and convenience of description, as a single fiber without cladding. Those skilled in the art will recognize, however, that principles of the present invention apply whether optical-fiber transmitter 54 is a single fiber or multiple-fiber bundle or array, with fiber or fibers clad or unclad.

Methods and arrangements for coupling laser radiation into optical-fibers or waveguides are well known to those skilled in the art to which the present invention pertains, and a description thereof is not necessary for understanding principles of the present invention. Accordingly, description and depiction of a laser radiation source and the manner in which it is coupled to optical-fiber transmitter 54 is not presented herein.

LEDs 46 direct visible light toward target 26 in a general direction indicated by arrow A (see FIG. 1) recognizing, of course, that light is actually emitted in a cone of rays about that general direction. Visible light from LEDs 46 entering target 26 is scattered within the target material. A portion of the scattered light is trapped within the target and directed along the target by total internal reflections, in what might be described as a light piping effect. A portion of this directed light is emitted from the target at the end thereof adjacent output-face 56 of optical-fiber transmitter 54 as indicated in FIG. 1 by arrows B. This light is emitted in the same general direction as laser radiation (indicated in FIG. 1 by arrows C) is emitted from output-face 56 of optical-fiber transmitter 54. This emission of visible light is enhanced somewhat by inclining the general emission direction of visible light from LEDs 46 toward the laser light emission direction as illustrated in FIG. 1.

Again, it should be noted that the term "emission direction" as applied to the laser radiation and visible light, applies to the general, here axial, direction of emission. Visible light and laser radiation are in fact emitted as cones of rays about this general direction, as illustrated. The angle of the cones is determined by the effective numerical apertures of target 26 and optical-fiber transmitter 54.

For a 1:1 imaging system, target 26 and output-face 56 of optical-fiber transmitter 54 are located at about a focal length of lens element 28 from that element. Accordingly visible light rays B and laser radiation rays C are collimated by lens 28 as illustrated collectively in FIG. 1 by arrows (D). The collimated visible light and laser radiation rays are then refocussed by lens-element 30, as illustrated by arrows BI and CI. Lens element 30 has the same focal length as lens element 28. This forms a 1:1 (unit magnification) image (not shown in FIG. 1) of the target and an image of the output-face of the optical-fiber transmitter in a common image plane at about a focal length of lens element 30 therefrom.

It should be noted here that alignment of output-face 56 and the end of target 26 need not be exact. Apart from normal alignment tolerances, there may be instances when some deliberate misalignment may be advantageous. One such instance would be to accommodate any axial chromatic aberration of optical system 27 when the wavelengths of target-illumination and laser radiation were sufficiently different. Further, it should be noted that optical system 27 is described here as a 1:1 imaging system, merely by way of example. It will be evident to one skilled in the art that optical system 27 may be a collimating, magnifying, demagnifying, or variable magnification system, wherein lens elements 28 and 30 may be replaced with a single or multiple elements of different shapes, focal length or spacing. Such changes to optical system may be made by one skilled in the art without departing from the spirit and scope of the present invention.

Figure 5:
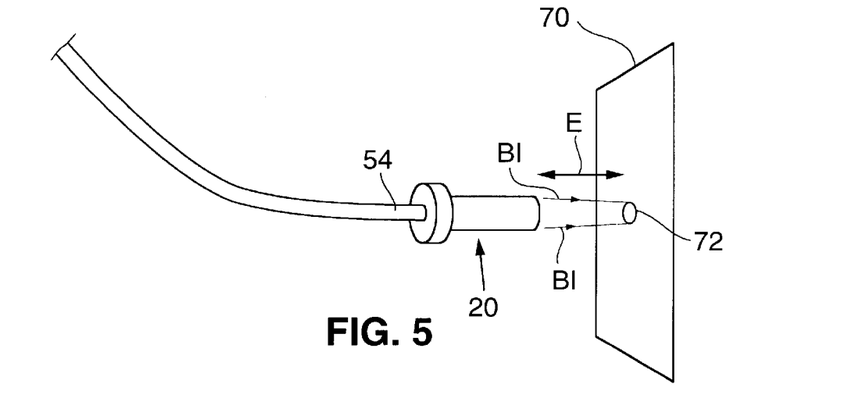
FIG. 5 schematically illustrates moving the apparatus of FIG. 1 toward or away from a surface to focus the target-image and laser radiation emitted from the output-face of the optical-fiber transmitter on the surface.
Figure 6:
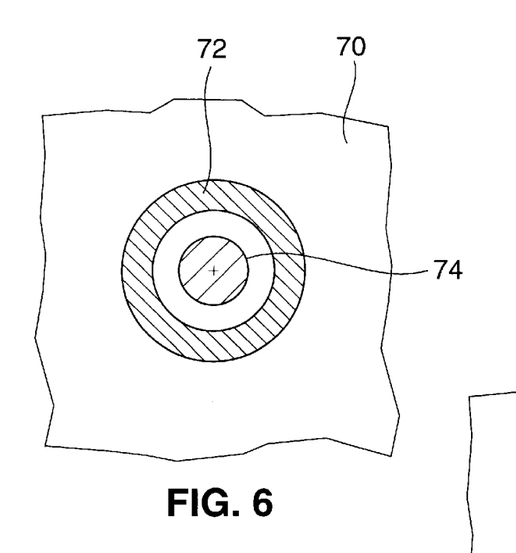
FIG. 6 schematically illustrates one form of focussed images of the target and output-face of the optical-fiber transmitter on the surface, wherein the target-image is circle surrounding the output face image.

Referring now to FIG. 5, whether or not the laser radiation is visible, apparatus 20 with optical-fiber transmitter 54 attached thereto, may be directed toward a surface 70 on which the laser radiation is to be incident and moved toward or away from the surface, as illustrated by arrows E, until a sharply focussed annular image 72 of the end of target 26 is observed. As illustrated in magnified form in FIG. 6, the target-image will surround an image 74 of end-face 56. Because of this, even if the end-face image is invisible, for example, because laser radiation emitted therefrom is invisible, or because the laser radiation is to be delivered in a pulsed or timed-continuous exposure only after its desired point or region of incidence on surface 70 is located, target-image 72 provides a reliable indication of that point or region of incidence. Further, by ensuring that the laser radiation image is in focus at each exposure, laser radiation flux can be delivered to the region of incidence in controlled and repeatable doses.

Figure 7:
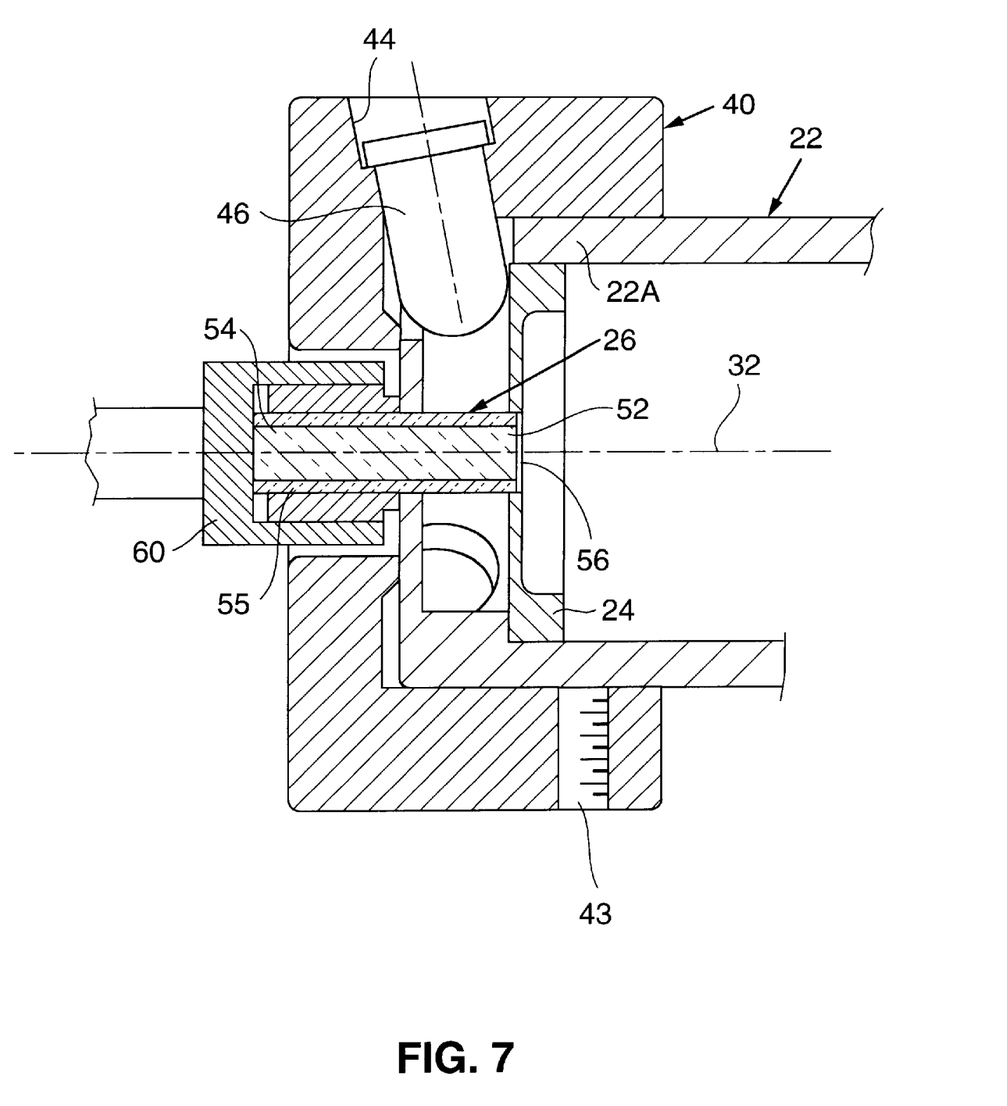
FIG. 7 schematically illustrates an arrangement for forming the target of FIG. 1 using a translucent, protective sheath of the optical-fiber transmitter.

Referring now to FIG. 7, an alternative method of forming target 26 for apparatus 20 is illustrated. Here a sheath 55 of optical-fiber transmitter 54 is formed from a translucent material which serves as a ferrule for an optical connector. One such optical connector is a ceramic-ferrule, ST™ type, available from AT&T Corporation. In such a case, exposed sheath covering distal end 52 of optical-fiber transmitter 54 within illuminator 40 forms target 26. Target support 24, in this case, serves only as a mask to prevent uncontrolled emission of light from LEDs 46 into optics housing 22.

Figure 8:
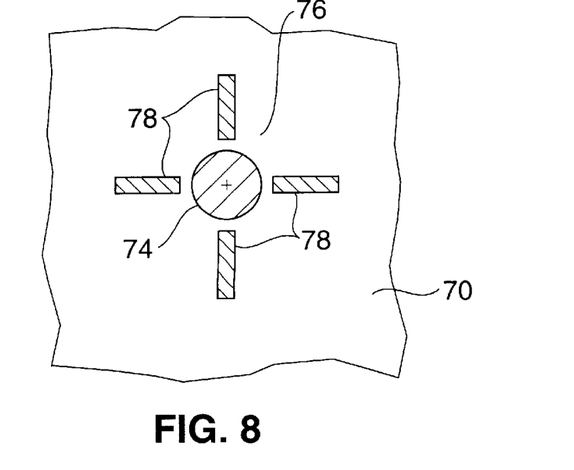
FIG. 8 schematically illustrates another form of focussed images of the target and output-face of the optical-fiber transmitter on the surface, wherein the target-image is in the form of "cross-hairs".

For certain applications wherein laser radiation is delivered in a very small spot it may be found desirable to provide a target image in the form of a reticle or "cross-hairs" which is often preferred for indicating a precise spot rather than encircling a region. Such an arrangement is depicted in FIG. 8, wherein a target image 76 surrounding end-face image 74 has four parts 78 orthogonally arranged to provide a cross-hair effect. Those skilled in the art will recognize without further illustration that such an image could be formed by placing a suitable mask on or adjacent the end of a cylindrical target such as 26 of FIG. 1.

Figure 9:
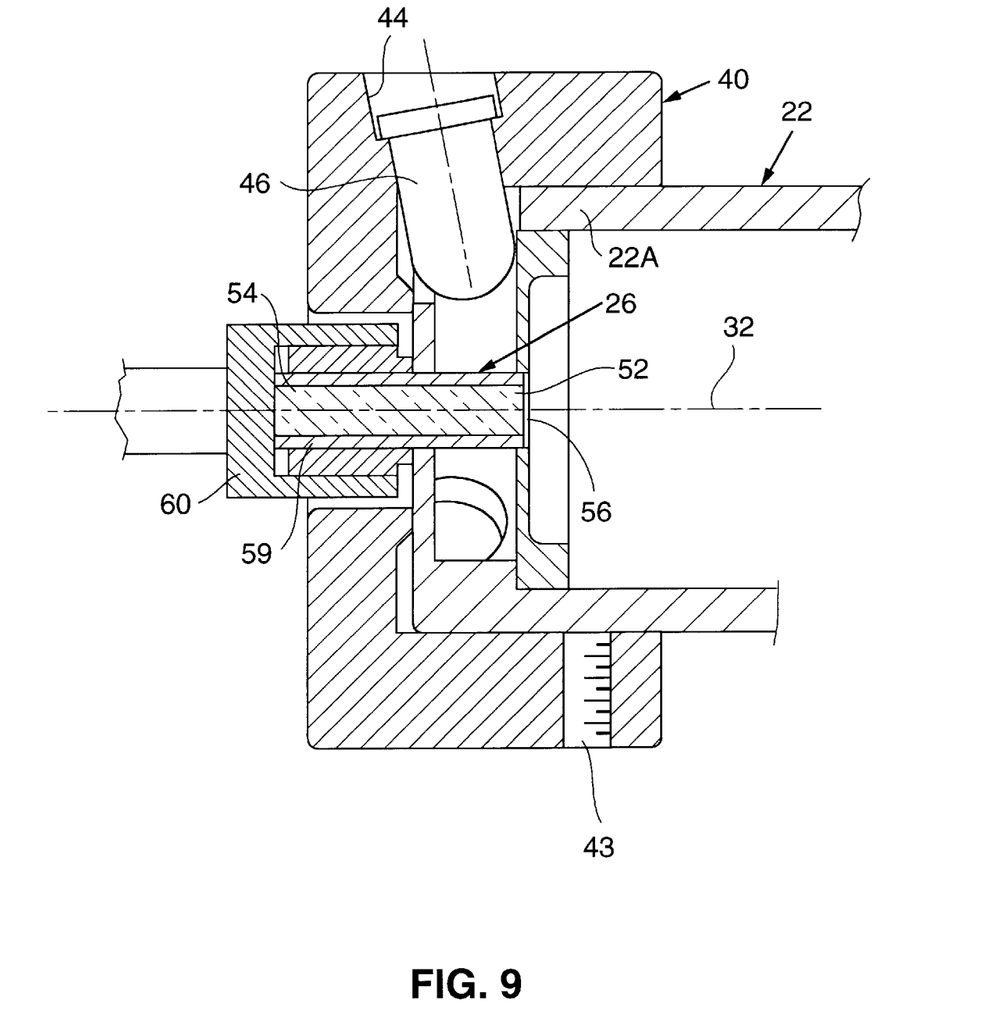
FIG. 9 schematically illustrates an arrangement for forming the target of FIG. 1 using the fiber cladding of an optical-fiber transmitter.

Referring now to FIG. 9 yet another target forming arrangement is illustrated. Here optical-fiber transmitter 54 is a single, clad fiber. Cladding 59 at output-end 52 of the optical fiber here serves as target 26. Cladding 59 may of course be completely transparent to visible light from LEDs 46. An advantage of this target arrangement is that a focussed target image (of the end of the cladding) may be formed essentially in contact with a focussed image of output-face 56 of optical-fiber 24, thereby providing a high degree of precision for the aiming system.

Figure 10:
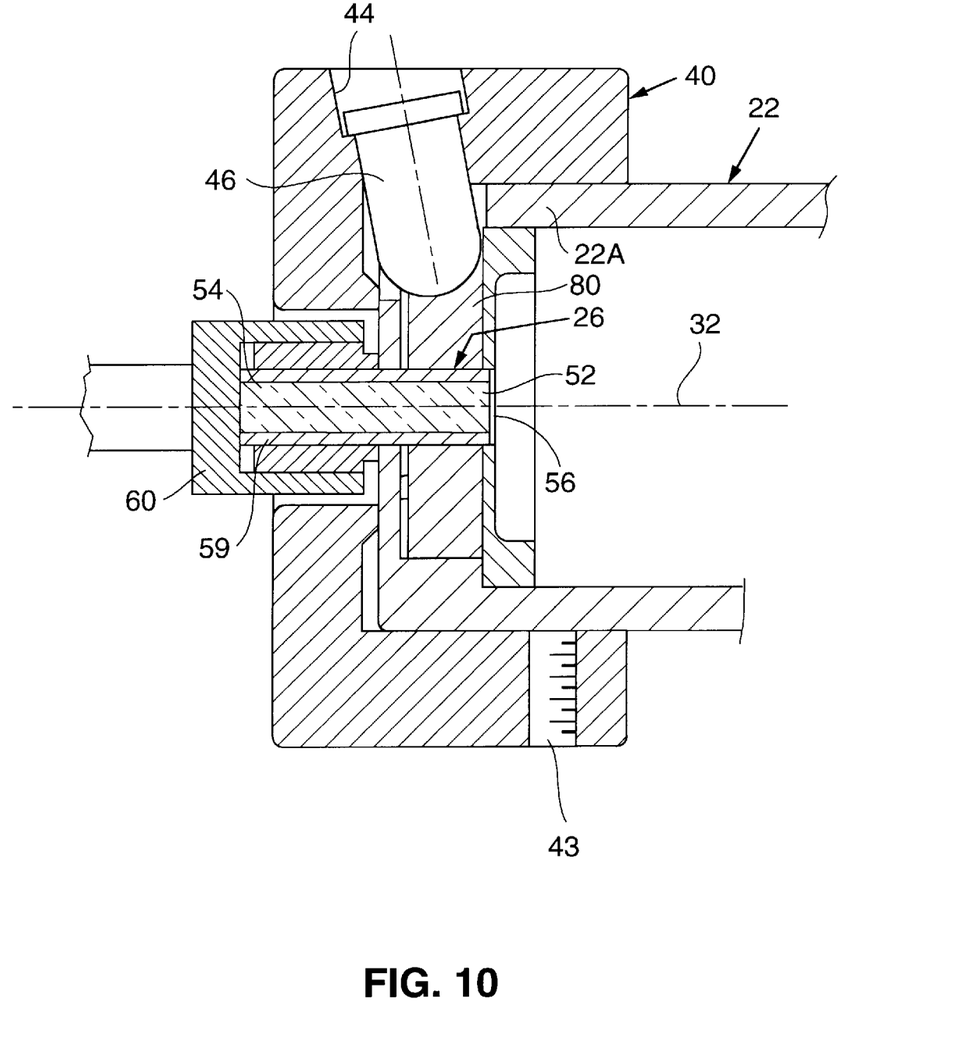
FIG. 10 schematically illustrates the arrangement of FIG. 9, additionally including an optical contact medium between the cladding and LEDs for illuminating the cladding.

A disadvantage of the arrangement, is that only a very small (relative to a translucent target) proportion of light entering the cladding is redirected by the cladding and escapes therefrom in the emission direction of laser radiation. This disadvantage can be at least partly remedied, as illustrated in FIG. 10, by providing an optical contact medium 80 between LEDs 46 and cladding 59. This contact medium may be conveniently provided by a washer of a transparent oil-filled elastomer material which has an elastic memory, can have a refractive index matched to the cladding material and has the property of being able to wet a glass surface with which it is placed in contact. The medium can thus provide a passage for light from LEDs 46 into cladding 59 essentially free of Fresnel losses. Further, the wetting of the glass occurs without permanent adhesion between glass and elastomer. This enables the optical contact to be made without permanently bonding optical-fiber transmitter 54 into illuminator 40.

While the present invention has been described as including an optical system for focussing laser radiation and providing a precise target-image, those skilled in the art to which the present invention pertains will recognize there may be applications wherein precise focus of laser radiation is not necessary. One such example is heat treatment of a non-biological material. For such applications, optical system 27 of apparatus 20 can be dispensed with. In the absence of optical system 27 housing 22 could be much shorter than depicted in FIG. 1, In the absence of an optical system 27, clearly a target-image would not be formed. Rays B of FIG. 1, when incident on a surface 70, would create an observable effect varying from a blurred annular illuminated area, when surface 70 is close to target 26, to a blurred disc-shaped area as the distance of surface 70 from target 26 increases. Nevertheless, the incident rays from the target would still provide the desired result of a visible indication of the incidence region of the laser radiation.

The present invention has been described as a preferred and other embodiments. The invention is not limited, however, to those embodiments described and depicted. Rather, the invention is defined by the claims appended hereto.

What is claimed is:

1. Apparatus for aiming and projecting laser radiation emitted from an output-face at an output-end of an optical-fiber transmitter, comprising:
   a target proximate the output-face of the optical-fiber transmitter;
   at least one light-source for emitting visible light, said light-source arranged proximate said target such that visible light emitted thereby is directly incident on said target in a direction transverse to the emission direction of the laser radiation from the optical-fiber transmitter; and
   said target and said light-source being arranged such that said target directs at least a portion of said visible light incident thereon in the emission direction of the laser radiation from the output-face of the optical-fiber transmitter in such a way that when the optical-fiber transmitter is directed toward a surface, said visible light directed by the target indicates an incidence point of the laser radiation on the surface.

2. The apparatus of claim 1, wherein said target is disposed around the output-end of the optical-fiber transmitter.

3. The apparatus of claim 2 wherein said target is a cylinder of translucent material surrounding the optical-fiber transmitter.

4. The apparatus of claim 3 wherein said cylinder of translucent material is formed by a sheath of said translucent material serving as a ferrule for a connector connecting the optical-fiber transmitter to the apparatus.

5. The apparatus of claim 1 wherein the optical-fiber transmitter is a clad optical-fiber and said target is the cladding of said clad optical-fiber.

6. The apparatus of claim 1 wherein the optical fiber transmitter is removably held in a fixed relationship with said target.

7. The apparatus of claim 1 further including an optical system of one or more optical elements, said optical system, said target, and said output-face of the optical-fiber transmitter arranged and aligned such that an image of said target and an image of the output-face of the optical-fiber transmitter are projected in a common image plane.

8. The apparatus of claim 7, wherein said target is disposed around the output-face of the optical-fiber transmitter, whereby said image of said target is disposed around said image of the output-face of the optical-fiber transmitter in said common image plane.

9. The apparatus of claim 1 wherein said at least one light source is a light-emitting diode.

10. The apparatus of claim 1, wherein said at least one light source is selected from a group of light sources selected from the group consisting of an incandescent light source, a diode-laser, and an electroluminescent panel.

11. The apparatus of claim 1 wherein there are a plurality of light sources directed at said target and generally equispaced therearound.

12. The apparatus of claim 11 wherein each of said light sources are light-emitting diodes.

13. The apparatus of claim 12 wherein light is emitted by said light emitting diodes in a direction inclined toward the emission direction of said the laser radiation.

14. Apparatus for aiming and projecting laser radiation emitted from an output-face at an output-end of an optical-fiber transmitter, comprising:
   a target held adjacent the output-end of the optical-fiber transmitter;
   at least one light-source for emitting visible light, said light-source arranged proximate said target such that visible light emitted thereby is incident on said target in a direction transverse to the emission direction of the laser radiation from the optical-fiber transmitter thereby illuminating said target; and
   an optical system of one or more optical elements, said optical system, said output-end of said optical-fiber transmitter and said target arranged and aligned such that said optical system projects an image of the output-face of the optical-fiber transmitter together with a visible image of said target such that when the optical-fiber transmitter is directed toward a surface and held at a predetermined distance from said surface, said target-image is visible thereon and indicates an incidence point of the laser radiation on the surface.

15. The apparatus of claim 14, wherein said optical system, said output-end of said optical-fiber transmitter and said target are arranged and aligned such that said target-image and output-face image are formed in a common image plane, whereby an observable degree of focus of the visible target-image on the surface indicates a corresponding degree of focus of the laser radiation on the surface.

16. The apparatus of claim 15, wherein said target is in the form of a cylinder having an inside diameter greater than outside diameter of the optical-fiber transmitter and a cylindrical axis aligned with the optical axis of said optical system, and the output-end of the optical-fiber transmitter is held axially aligned within said target with its output-face aligned with an end of said target such that said visible target-image appears on the surface as a circle, the circle surrounding the incidence point of the laser on the surface.

17. The apparatus of claim 14, wherein said target is arranged such that said visible image thereof is in the form of cross-hairs.

18. The apparatus of claim 14, wherein said optical system is one of a magnifying optical system, a reducing optical system and a variable magnification optical system.

19. The apparatus of claim 14, wherein said target is removably held adjacent said optical-fiber transmitter.

20. Apparatus for aiming and projecting laser radiation emitted from an output-face at an output-end of an optical-fiber transmitter, comprising:

a cylindrical target held surrounding the output-end of the optical-fiber transmitter with an end of said cylindrical target proximate said output-face of said optical-fiber transmitter;

a plurality of light emitting diodes arranged around said target for illuminating said target with visible light in a direction transverse to the emission direction of the laser radiation from the optical-fiber transmitter; and an optical system of one or more optical elements, said optical system, said output-face of said optical-fiber transmitter and said end of said target arranged and aligned such that said optical system projects an image of the output-face of the optical-fiber transmitter together with a visible image of said end of said target, whereby when the optical-fiber transmitter is directed toward a surface, said target-end-image is visible thereon as a annulus, said annulus surrounding an incidence point of the laser radiation on the surface.

21. Apparatus for aiming and projecting laser radiation emitted from an output-face at an output-end of a clad optical fiber, comprising:

one or more light sources arranged around the output- end of said optical-fiber for illuminating cladding thereof with visible light in a direction transverse to the emission direction of the laser radiation in such a way that a portion of said light is transmitted along the cladding and escapes therefrom in the emission direction of the laser radiation; and an optical system of one or more optical elements, said optical system and the output-face of the optical-fiber arranged and aligned such that said optical system projects an image of the output-face of the optical-fiber together with a visible image of the cladding, whereby when the optical-fiber is directed toward a surface and held at a predetermined distance therefrom, said cladding image is visible thereon as an annulus, said annulus surrounding an incidence point of the laser radiation on the surface.

22. The apparatus of claim 21, further including means for making optical contact between said one or more light sources and the cladding.

23. An apparatus connectable to the delivery end of an optical fiber, said optical fiber emitting a beam of laser radiation out of the end face thereof, said apparatus facilitating the positioning and focusing of the laser beam, said apparatus comprising:

a housing removably mountable on the delivery end of the fiber;

a target configured to fit around the outer circumference of the delivery end of the optical fiber;

an illuminator mounted in said housing and arranged proximate said target such that visible light emitted thereby is incident on an outer surface of the target in a manner so that a portion of the light exits an end face of the target in the same general direction as the laser beam exiting the end face of the optical fiber; and a focusing system mounted in the housing for focusing both the laser beam emitted from the fiber and the visible light emitted from the target to a common image plane beyond the end of the housing.

24. An apparatus as recited in claim 23, wherein said target is defined by a cylinder of translucent material surrounding the delivery end of the fiber.

25. An apparatus as recited in claim 23, wherein said target is defined by the cladding of the optical fiber.

26. An apparatus as recited in claim 23, wherein the illuminator is a light emitting diode.

\* \* \* \* \*